United States Patent [19]

Casero, deceased

[11] Patent Number: 5,340,579
[45] Date of Patent: Aug. 23, 1994

[54] METHOD OF TREATING DERMATOLOGICAL CONDITIONS

[75] Inventor: Riccardo Casero, deceased, late of Como, Italy, by Patrizia Magnasco Casero, executor, Francesca Margaret Casero, Elisabetta Giovanna, heirs

[73] Assignee: Farmaka S.r.l., Grandate, Italy

[21] Appl. No.: 541,119

[22] Filed: Jun. 20, 1990

Related U.S. Application Data

[63] Continuation-in-part of Ser. No. 83,944, Aug. 4, 1987, abandoned, which is a continuation of Ser. No. 797,685, Nov. 13, 1985, abandoned.

[30] Foreign Application Priority Data

Nov. 20, 1984 [IT] Italy ............................. 23676 A/84

[51] Int. Cl.$^5$ .................... A61K 35/00; A61K 37/00; A61K 37/02; A61K 37/10
[52] U.S. Cl. ........................................ 424/114; 514/2; 514/8; 514/21; 514/336; 514/844; 514/847; 514/858; 514/859; 514/860; 514/861; 514/862; 514/863; 514/864; 514/865
[58] Field of Search ................ 514/2, 8, 21, 336, 847, 514/844, 858–865; 424/114, 115–117, 70

[56] References Cited

U.S. PATENT DOCUMENTS

| | | | |
|---|---|---|---|
| 3,887,703 | 6/1975 | Manoussos et al. | 424/180 |
| 4,303,676 | 12/1981 | Balazs | 424/359 |
| 4,504,494 | 3/1985 | Grollier et al. | 514/544 |

FOREIGN PATENT DOCUMENTS

| | | |
|---|---|---|
| 158706 | 12/1981 | Japan. |
| 1198005 | 3/1968 | United Kingdom. |
| 1283892 | 8/1972 | United Kingdom. |
| 200232A | 2/1979 | United Kingdom. |

OTHER PUBLICATIONS

The Merck Index, 19th Ed., Merck and Co., Rahway, N.J. 1976, p. 624, entry No. 4634.
*Clinical Pharmacology Research,* "Assessment of the Effects of a Topical Product Containing Glycosaminoglycans in Cutaneous Hydration", Berardesca, E. et al.

*Primary Examiner*—F. T. Moezie
*Attorney, Agent, or Firm*—Browdy and Neimark

[57] ABSTRACT

A method is provided for treating dermatological conditions by binding and blocking 5-a-dihydrotestosterone receptors comprising applying to the skin an effective amount of composition comprising:

(a) from about 0.1% to about 2.0% by weight of mucopolysaccharides free of proteins and having a pH ranging from about 5 to 7.5 in aqueous solution, a rotary power between about to +15, and a sulfur content greater than 6%;

(b) from about 1% to about 3% by weight of an aqueous extract of human umbilical cord free from sulfur and having a DH of from about 5 to about 7, a viscosity of 30° C. of from 10 to 25 centistokes, a hyaluronic acid titre of from about 500 to about 700 mg/dl, and an ash content of less than about 0.5%;

(c) from about 0.05 to about 0.08% by weight of tetrahydrofurfuryl nicotinate; and (d) pharmaceutically and cosmetically acceptable vehicles and excipients.

This method is particularly useful in treating dermatological conditions such as acne, wrinkles, lipodiystrophies, dermosclorosis, androgenic alopecia, hypertrichosis, and the like.

6 Claims, 3 Drawing Sheets

METHOD OF TREATING DERMATOLOGICAL CONDITIONS

This present invention is a continuation-in-part of Ser. No. 07/083,944, filed Aug 4, 1987, which is a continuation of application Ser. No. 06/797,685, filed Nov. 13, 1985, both are now abandoned.

FIELD OF THE INVENTION

The present invention relates to a method for treating dermatological conditions by binding and blocking 5-α-dihydrotestosterone receptors. More particularly, the present invention relates to treating conditions such as acne, wrinkles, lipodystrophies, dermosclerosis, androgenic alopecia, hypertrichosis, and one like.

BACKGROUND OF THE INVENTION

It is known that cutis, because of the particular functions it has, is structured in a particular way and is substantially comprised of two superimposed layers, namely, the underlying derma and the epidermis forming the external surface of cutis.

As epidermis is devoid of blood vessels, even if it must carry out many of the most remarkable functions of the skin, such as the protective, secretive, thermoregulating, respiratory functions, and so on, metabolic impairments often occur, affecting its appearance and jeopardizing its functions, which may often be serious.

It is also known that hair, as the essential Dart of the human piliferous apparatus, is planted in epidermis, so that it also shares in a very considerable way its vicissitudes and deficiencies. Therefore, loss of hair is a more and more frequent phenomenon both in men and in women, also in situations which are not typically pathological. The multifactorial aetiogenesis of such hair loss, which may be related to stress, atmospheric pollution, emotional factors, use of strongly detergent shampoos, for example, is always related to a morphological alteration in the connective tissue surrounding the hair bulb which is determined, inter alia, by the decrease of specific acidic mucopolysaccharides such as heparin, hyaluronic acid, and A, B, C, chondroitinsulfates in the connective tissue itself, with attendant dehydration, aging of the tissue, and dekeratinization, together with fragility and poor elasticity of the hair, and finally sclerosis and death of the hair bulb.

Hair growth is influenced by hormones for at least two major evolutionary reasons. One is so that the heat-conserving pelage can be changed to match the season. The other is so that the growth of sexual hair and production of scent from the associated glands can be restricted to the adult period.

It is possible that remnants of the first function are detectable in humans, for there are some indications of seasonal change, and there is clear evidence that the thyroid hormone has a profound effect on hair growth. Moreover, post-partum hair loss appears to be a consequence of hormonal changes in pregnancy and may well be analogous to the moult which follows parturition in some other mammals.

However, of paramount importance is the role of androgens in promoting growth of the beard in males, and of the pubic and axillary hair in both sexes, as is the paradoxical fact that hereditary male pattern baldness is androgen-dependent. Testosterone is carried in the human plasma attached to sex hormone binding globulin, and only about one percent is free to enter cells and become bound to intracellular receptors. There is some question as to whether the response of hair follicles, like that of the prostate, requires 5 α-reduction of the androgen, and whether the critical factors in male pattern alopecia, female-diffuse alopecia, and hirsutism are abnormally high plasma androgen, low sex hormone binding globulin, enhanced 5 α-reductase, enhanced binding by the intracellular receptor, or some other yet undiscovered mechanism.

Androgens are mainly produced in steroid producing glands. Additionally, they are formed in the body periphery from precursors such as DHIA and androstendione. In the ovaries they play an important role as biosynthetic intermediates for the synthesis of estrogens as well as for folliculogenesis. If this o process is disturbed, ovarian androgen secretion often is increased. Under clinical conditions, glandular androgen production is calculated best by measuring the steroid output in the effluent of the adrenals and gonads after catheterization of the glandular venes. Functional tests are less informative, and can occasionally be misleading. On the basis of androgen measurements in the glandular effluents of 80 androgenized women, increased androgen secretion comes in about half of the cases either form the ovaries or the adrenal glands and in the other half, from both glands.

Androgens in the blood are predominantly bound to sex hormone binding globulin and albumin. Just 0.5–2.0% of blood testosterone is present in the free, unbound form. Only this unbound blood androgen is believed to be biologically active. Androgenic alopecia is often associated with other signs of andro-genization. It is an obligatory symptom in severe virilism due to a massive increase in androgen production. In these cases, ablative surgery or suppression of the androgen excess by other means, such as by corticoids, rather than treatment by antiandrogens are the methods of first choice.

Male hormones affect human sebaceous glands and hair follicles. Skin conditions, such as male-pattern baldness, ache, hirsutism, and seborrhea, are attributed to over-androgenicity.

There are dramatic changes in hair growth at puberty which are selectively mediated by testosterone or by dihydrotestosterone. The characteristic increase of hairiness at puberty is not due to the formation of new follicles, as there is no neogenesis of hair follicles in the human. Rather, the increased hairiness is due to the conversion of small terminal follicles to large terminal follicles. In the axilla and lower public triangle, this conversion is mediated by testosterone or androstenedione. In all other regions, this conversion is mediated by dihydrotestosterone. Paradoxically, dihydrotestosterone also mediates the reverse process, namely, the miniaturization of large terminal follicles into small terminal follicles. Such physiological miniaturization occurs with the reshaping of the frontal hairline from a straight hairline to an M-shaped hairline. This occurs in all men and in the majority of women. In androgenic alopecia, the miniaturization process extends to include all genetically marked follicles. In the male, this may include all except the hair follicles along the peripheral margins of the scalp. In the female, the genetically marked follicles are scattered diffusely over the scalp with preservation of the frontal hairline.

The importance of the skin as an androgen target organ and the influence of androgens on hair growth are most convincingly demonstrated by two forms of male pseudohermaphroditism, testicular feminization and 5-α-reductase deficiency, in which the influence of androgens is lacking to different degrees.

It has been found that the administration of testosterone to the AGA mouse resulted in a patterned hair loss beginning at the dorsal head region and extending posteriorly towards the mid-dorsum over a three month period. Hair loss was characterized by a very small decrease in the growth phase (anagen), and a markedly prolonged duration of the resting phase (telogen). Alopecia in this model can be prevented by the administration of potent 5α-reductase and androgen receptor blocking agents, such as progesterone, cyproterone acetate, or spironolactone. Various vasodilating drugs, which are reported to produce hypertrichosis as a side effect when given to humans, were tested in testosterone-treated AGA mice by oral administration at a dose of 10 mg/kg. Minoxidil and diazoxide inhibited the testosterone induced alopecia at concentrations of 2% and 5%.

It is known that the female sexual hormones antagonize the masculine hormones at the peripheral target androgenosensible tissue. Munteanu et al. attempted to use progesterone in the local treatment of seborrheic alopecia. Progesterone was chosen because it is a strong inhibitor of the testosterone-blocking 5α-reductase and in this manner hinders the reduction of testosterone into 5α-dihydrotestosterone that produces a gene depression and consequently a follicle atrophy of the hairs of the head. In this way, the anagenesis phase of the hair is prolonged, in which the androgenetic alopecia is very short. Progesterones resorbed by the skin are concentrated within the hair follicle. No hormonal disorders and no androgenic effects were observed.

The most common form of hair loss is male-pattern alopecia, in which hair anagen (hair growth stage) gradually shortens and regenerated hair becomes thinner and shorter generation by generation in the temporal and parietal regions. It has been well established that such a phenomenon cannot occur without androgen.

The pathology of male-pattern alopecia is that the effect of androgen on the scalp expands sebaceous crypts and simultaneously shortens the hair cycle, namely, the cycle of hair life. In other words, alopecia is a phenomenon where a person's hair, which was originally long and thick, becomes thinner and shorter with every hair cycle.

It is known that, among androgens presenting the above effect on local dermal areas, 5 α-dihydrotestosterone (5 α-DHT) plays a principal role, and that 5α-DHT is produced through conversion from testosterone with the assistance of an enzyme, 5α-reductase, in sebaceous crypts or dermis fibroblasts.

Previously, in order to prevent aging of cutis and, particularly, hair loss, a number of different therapies have been proposed, including the local use of degreasing, rubefacient and vasodilating agents, polyvitaminic compositions, and vegetable extracts of different kinds, as well as mucopolysaccharide extracts with unspecified compositions and activity (with particular reference to the anticoagulant and lipasemic activities, which are closely correlated and interdependent activities) alone or in combination. However, none of these compounds has ever faced in a rational way, and consequently solved, the problem of physiological hydration of cutis and of the tissue surrounding the hair bulb which is an essential condition for the vitality of the bulb itself and thus of the hair.

Even if the use of sulfomucopolysaccharides, which notoriously possess hydrophilic properties, is already known, it is likewise known that these compounds usually are not substantially absorbed through cutis.

SUMMARY OF THE INVENTION

It is an object of the present invention to overcome the aforementioned deficiencies of the prior art.

It is another object of the present invention to provide a composition and method for provoking an facilitating the cutaneous absorption of mucopolysaccharides.

It is another object of the present invention to provide a method of binding and blocking 5-α-dihydrotestosterone receptors by topical application of extract of human unbilical cord.

It is a further object of the present invention to provide method to promote the hydration and trophism of skin, and particularly of hair.

According to the present invention, the cutaneous absorption of mucopolysaccharides, and thus blocking of 5-α-dihydrotestosterone receptors, can be facilitated by mixing them with an umbilical cord extract which is notoriously rich in chondroitinsulfates and hyaluronic acid, obtained under particular conditions.

The present invention is based on the finding that an extract of umbilical cord, besides possessing its own high hydrophilic and hydrating properties, enhances the absorption of the essential mucopolysaccharides by the skin, because of the presence of the peptide chains of proteohyaluronic acid contained therein, which, by promoting an increase in the peripheral blood microcirculation, allows an effective absorption of the active ingredient. This extract of umbilical cord binds and blocks 5-α-testosterone receptors, and treats a number of dermatological conditions, including acne, wrinkles, lipodystrophics, dermosclerosis, androgenic alopecia, hypertrichosis, and the like A further problem solved by the present invention is that of selecting the acidic mucopolysaccharides which must be supplied to the skin and must be such as to correct the typical deficiency of these substances occurring concomitantly with hair loss and aging of cutis. The mucopolysaccharides chose for topical application, furthermore, must act, through their clarifying (i.e., anticoagulating and normolipemising) activity, as regulators for the sebaceous secretion which is one cause of weakening of the hear and of sclerosis of the hair bulb, all causes which lead to common baldness or androgenetical or seborrheical alopecia.

The complex of extractive acidic mucopolysaccharides of animal origin according to the present invention is rich in chondroitinsulfates and heparin-like substances and is characterized by the following essential analytical parameters:

| pH in aqueous solution about 5 to about 7.5 | |
|---|---|
| rotatory power | 0 to about +15° |
| proteins | absent |
| total nitrogen | ≦4.5% |
| sulfur | ≧6% |
| inorganic phosphorus | ≦0.5% |
| hexuronic acids | ≧20% |
| hexosamines | ≧20% |
| anticoagulating activity | about 40–50/mg I.U. USP, XX |

The extract of umbilical cord to be mixed with the mucopolysaccharides according to the present invention is an aqueous extract of human or animal umbilical cord containing, on the average, 5 to 7 g/liter of hyaluronic acid, principally in the form of proteohyaluronic acid (proteoglycan), and containing, moreover, g chondroitinsulfate. The hyaluronic acid, as contained in this extract, exhibits a molecular weight of between about 2.5 and 3 million.

An aqueous extract of human umbilical cord exhibits the following essential analytic features:

| viscous, transparent, slightly yellowish solution | |
| --- | --- |
| pH | about 5 to about 7 |
| viscosity at 30° C. | about 10 to about 25 centistokes |
| residue at evaporation | about 2 to 3% |
| hyaluronic acid titre | about 500 to about 700 mg/dl |
| ashes | about 0.1 to 0.5% |
| sulfur | absent |
| proteins | about 0.5 to about 1.0% |
| total nitrogen | about 0.15 to about 0.30% |
| aminic nitrogen | about 0.10 to about 0.20% |
| hexosamines | about 0.010 to about 0.050% | obtained as follows:

A certain quantity of umbilical cord is washed with water, crumbled by means of a triturator, and conveyed into a mixer, to which twice the amount of water as tissue, by volume, is added. The aqueous mush so obtained is milled, and the entirety is mixed at a low temperature. The mixed suspension is then filtered and the filtrate is concentrated at reduced pressure and low temperature.

4.5% of methyl-para-hydroxybenzoate and 0.5% of propylpara-hydroxybenzoate are separately dissolved in a volume of ethanol equivalent to 5% by volume of the concentrated solution. The two solutions are mixed and filtered, and the filtrate is then sterilized by filtration through a membrane.

The sterilized solution is then closed into hermetic vessels for subsequent use.

DETAILED DESCRIPTION OF THE INVENTION

Figure 1:
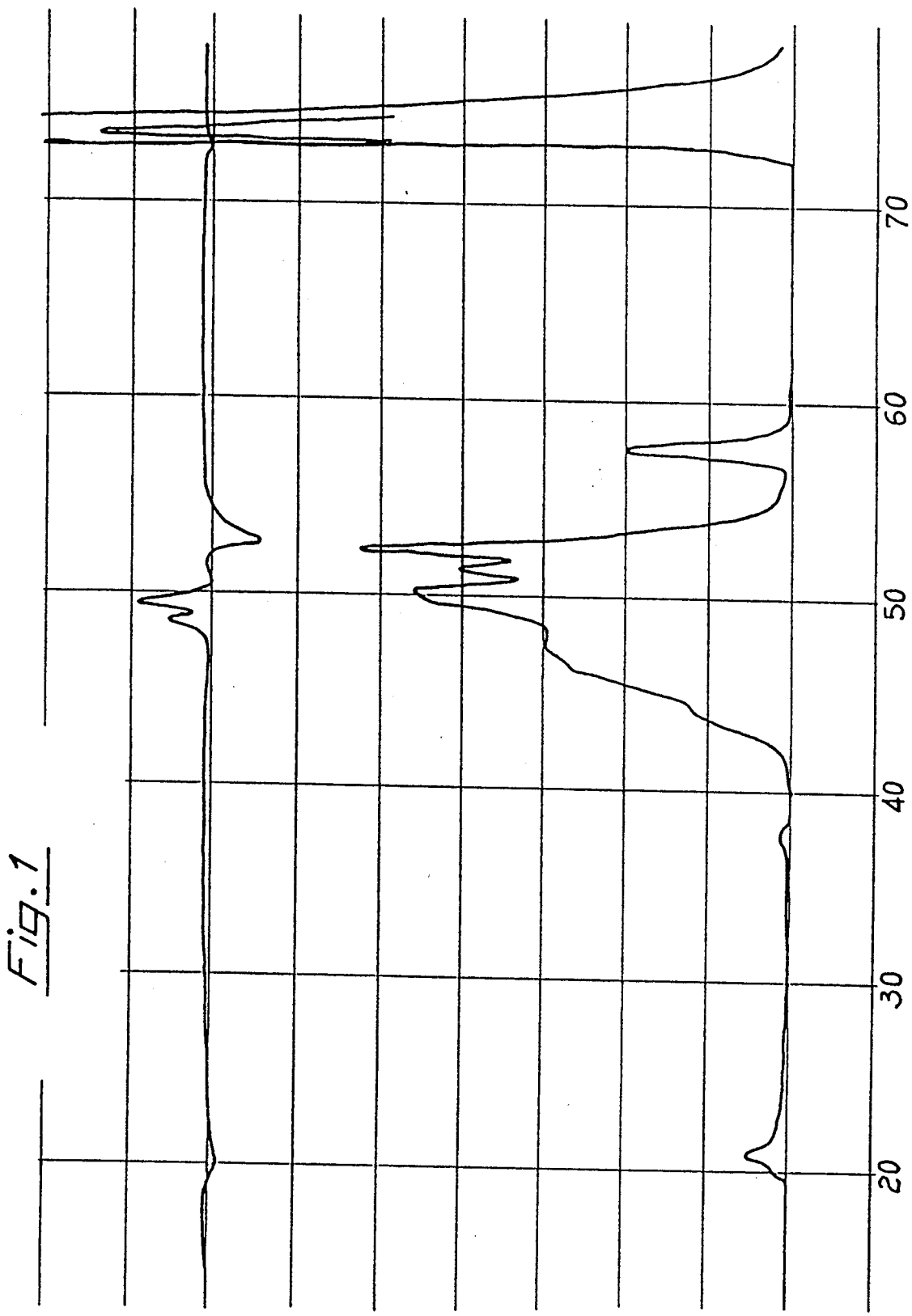
FIGS. 1 shows the graphs obtained from two samples of extract of umbilical cord according to the present invention by high speed gas chromatography with a mobile phase consisting of an aqueous solution of 0.1 M KCl buffered to pH 7.0 with a solution of phosphate 1/15 M.
Figure 2:
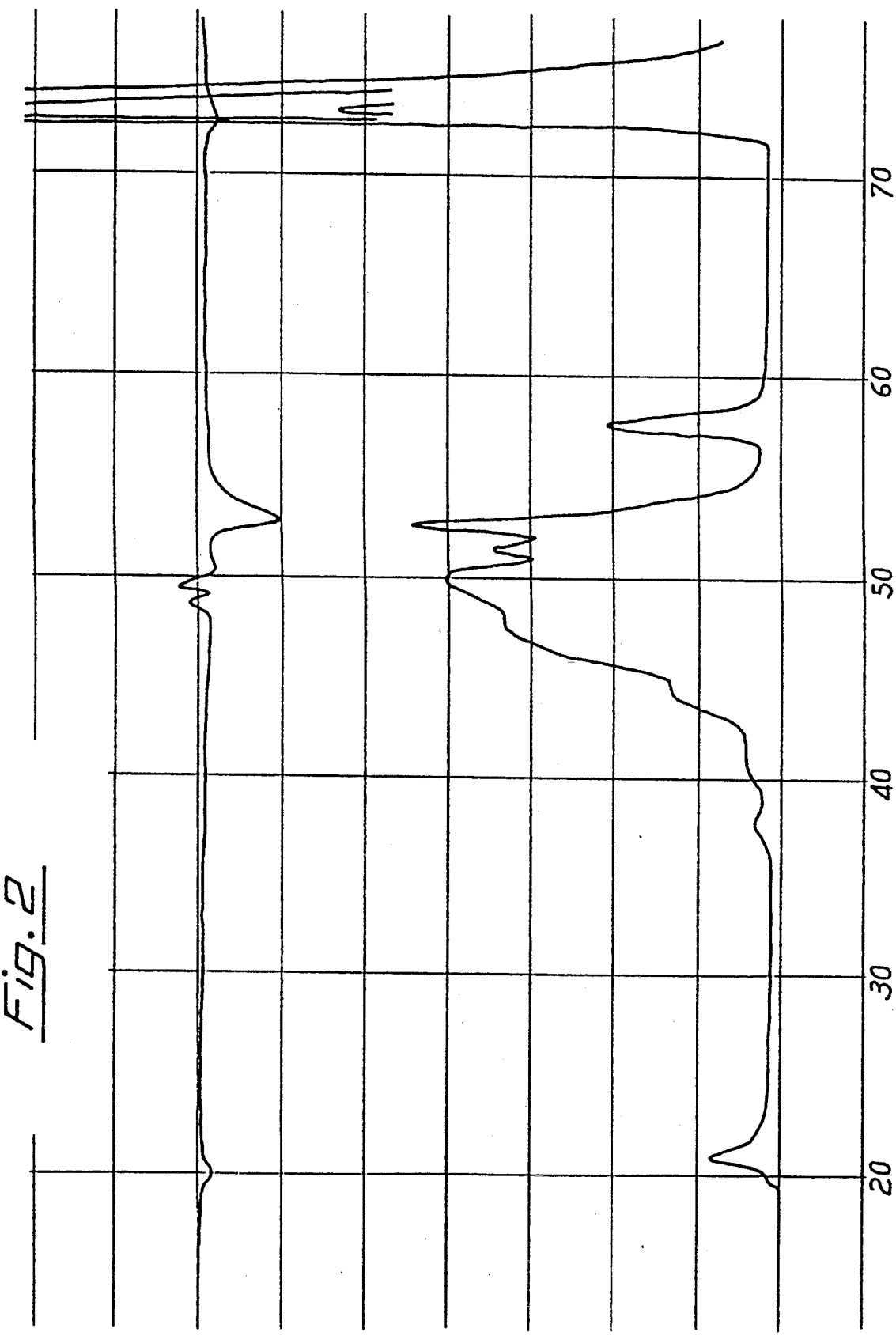
FIG. 2 shows the graphs obtained from two samples of extract of umbilical cord according to the present invention by high speed gas chromatography with a mobile phase consisting of an aqueous solution of 0..1 M KCl buffered to pH 7.0 with a solution of phosphate 1/15 M.
Figure 3:
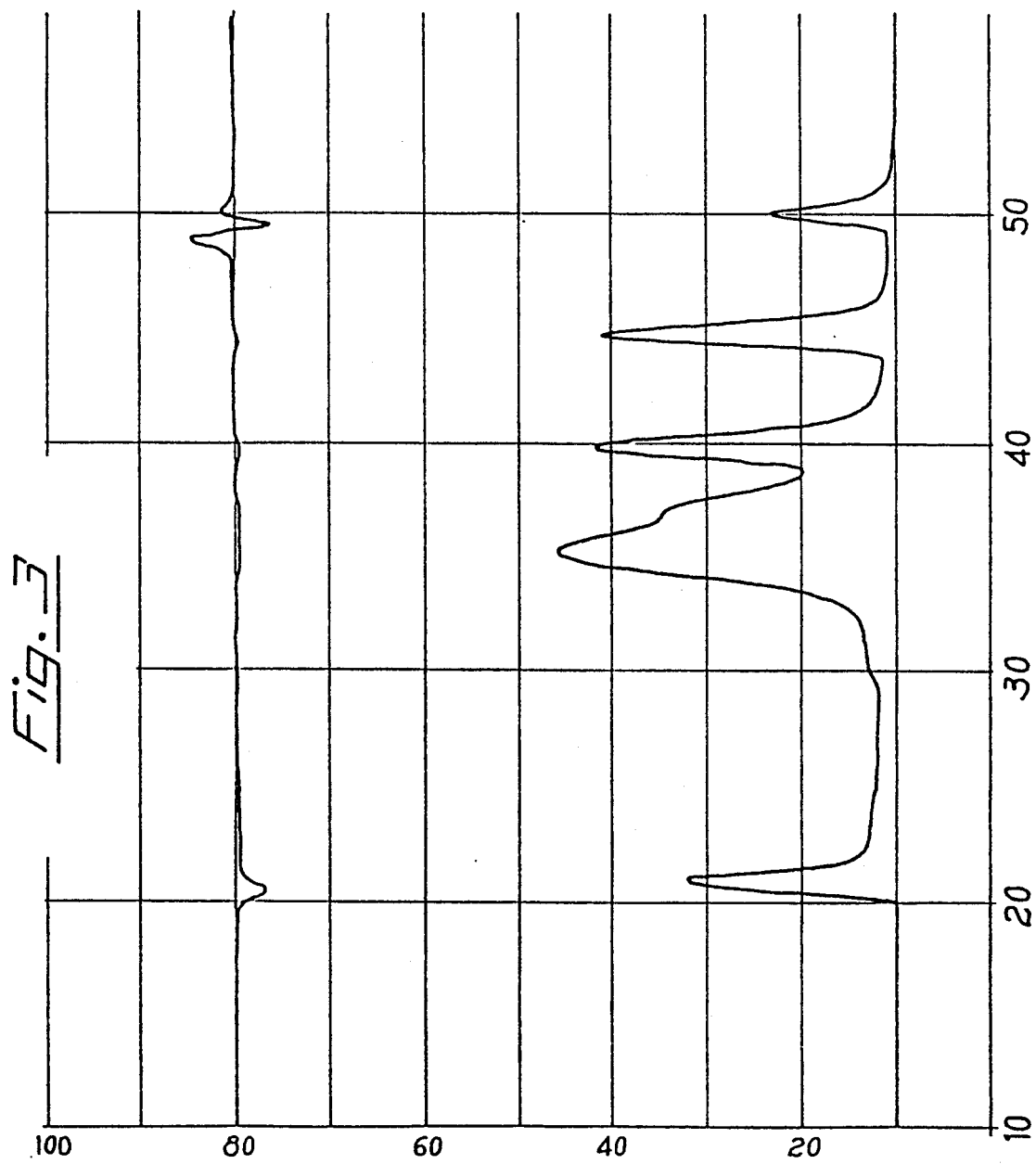
FIG. 3 shows the gas-chromatographic graph obtained form a standard solution containing dextran blue 2000, gamma globulin, lactalbumin, egg albumin, myoglobulin, and alanine in the same operational conditions.

The following non-limiting examples illustrate the particular properties of moisture retention shown by extracts of human umbilical cord which have been used in the formulations according to the present invention, in comparison with similar properties shown by other known substances having similar characteristics.

EXAMPLE 1

The tests were carried out using the following materials:

A) Extract of human umbilical cord (HA) with residue at evaporation=2.23%

B) Solution of sodium chondroitinsulfate (CS-Na) with residue at evaporation=3.0%

C) Solution of sodium pyrrolidonecarboxylate (PCA-Na) with residue at evaporation=3.0%.

Carefully weighted samples of 20 g of A, B, and C, representatively placed in glass capsules having an inside diameter of 85 mm and a depth of 20 mm were placed into a dried adjusted at 30° C. and 80% relative humidity. The prepared samples were then weighed every 24 hours so as to evaluate the undergone weight changes.

The hydrating effect was obtained on the basis of the following ratio:

$$\text{Hydrating effect (\%)} = \frac{\text{Residual water}}{\text{Residue at evaporation}} \times 100$$

TABLE 1

| | SAMPLE | 1 | 2 | 3 | 4 | 5 |
| --- | --- | --- | --- | --- | --- | --- |
| A | Residue at evaporation | 446 mg | 446 mg | 446 mg | 446 mg | 446 mg |
| | Residual water | 4254 mg | 1854 mg | 554 mg | 554 mg | 554 mg |
| | Hydrating effect (%) | 953.8% | 415.7% | 124.2% | 124.2% | 124.2% |
| B | Residue at evaporation | 600 mg | 600 mg | 600 mg | 600 mg | 600 mg |
| | Residual water | 1400 mg | 200 mg | 100 mg | 100 mg | 100 mg |
| | Hydrating effect (%) | 233.3% | 33.3% | 16.6% | 16.6% | 16.6% |
| C | Residue at evaporation | 600 mg | 600 mg | 600 mg | 600 mg | 600 mg |
| | Residual water | 4800 mg | 2400 mg | 500 mg | 447 mg | 363 mg |
| | Hydrating effect (%) | 800.0% | 400.0% | 83.3% | 74.5% | 60.5% |

EXAMPLE 2

Tests similar to those of Example 1 were carried out on the same substances A, B, and C and, furthermore, on the following substance:

DO A solution of sorbite (SORB) with residue at evaporation=3%

Some samples of 0.1 g of substances A, B, C, and D, respectively collected into glass vessels with a diameter of 30 mm and depth of 30 mm, were put into a drier in the presence of a saturated solution of $K_2 CO_3$. The samples so treated were then weighted after 1, 2, 3, 5, 8, 24, 32, and 48 hours so as to record the weight changes.

The hydrating effect was calculated on the basis of the ratio reported in Example 1. The results obtained are shown in Table 2 and schematically illustrated in FIG. 5.

TABLE 2

| TIME | SAMPLE | | | | |
|---|---|---|---|---|---|
| 0 hours | Residual water (mg) | 912.9 | 931.5 | 989.7 | 986.4 |
| | Residue at evaporation | 20.25 | 28.81 | 30.61 | 30.51 |
| 1 hours | Residual water (mg) | 901.2 | 921.7 | 980.7 | 975.8 |
| | Hydrating effect (%) | 4450.5 | 3199.3 | 3203.9 | 3198.6 |
| 2 hours | Residual water (mg) | 885.2 | 909.4 | 969.8 | 967.4 |
| | Hydrating effect (%) | 4371.0 | 3156.6 | 3168.3 | 3171.1 |
| 3 hours | Residual water (mg) | 868.5 | 897.3 | 957.6 | 952.5 |
| | Hydrating effect (%) | 4288.6 | 3114.6 | 3128.5 | 3122.3 |
| 5 hours | Residual water (mg) | 836.9 | 872.6 | 933.0 | 927.4 |
| | Hydrating effect (%) | 4132.5 | 3028.9 | 3048.1 | 3039.9 |
| 8 hours | Residual water (mg) | 788.1 | 830.4 | 892.3 | 883.9 |
| | Hydrating effect (%) | 3892.0 | 2882.4 | 2915.1 | 2897.3 |
| 24 hours | Residual water (mg) | 555.6 | 591.5 | 657.4 | 658.1 |
| | Hydrating effect (%) | 2743.4 | 2053.2 | 2147.7 | 2157.2 |
| 32 hours | Residual water (mg) | 488.2 | 476.5 | 537.6 | 531.0 |
| | Hydrating effect (%) | 2213.0 | 1654.0 | 1756.3 | 1740.6 |
| 48 hours | Residual water (mg) | 225.4 | 244.5 | 305.7 | 295.0 |
| | Hydrating effect (%) | 1112.8 | 848.7 | 998.7 | 967.0 |

From the above data it is clear that the extract of human umbilical cord, used according to the present invention, shows water retention effects which are decidedly higher than those of substances already known for their properties of absorbing and retaining water.

The mixture of umbilical cord extract and mucopolysaccharide complex according to the present invention normally contain other active ingredients, adjuvants, or additives, such as, preservatives, wetting agents, fungicidal agents, surfactants, bactericides, vitamins, pH regulating agents, etc., all of which are conventionally known in the art.

Examples of presently preferred formulations according to the present invention are given hereinafter.

EXAMPLE 3

| Lotion for treating scalp for androgenitic or seborrhec alopecia | | |
|---|---|---|
| Extract of umbilical cord | mg | 120.00 |
| Mucopolysaccharide complex | mg | 8.58 |
| Tetrahydrofurfuryl-nicotinate | mg | 4.50 |
| Propylene gylcol | mg | 0.20 |
| Methylparaben | mg | 8.10 |
| Propylparaben | mg | 3.90 |
| Sorbic acid | mg | 6.00 |
| Sodium pantothenate | mg | 6.00 |
| Biotin | mg | 0.15 |
| Ethanol | mg | 0.44 |
| Perfume | mg | q.s |
| Distilled water | mg | q.s to ml 6.00 |

The above given formulation is prepared in the form of vials for topical application directly to the scalp.

| Face moisturizing lotion | | |
|---|---|---|
| Mucopolysaccharidic complex | g | 0.3 |
| Extract of umbilica cord | g | 2.0 |
| dl-α-tocopherol | g | 0.5 |
| Ethanol | g | 13.0 |
| Glycerine | g | 2.0 |
| Propylene glycol | g | 5.0 |
| Polyoxyethylene sorbitane monoaurate (20 E.0.) | g | 2.0 |
| Polyethylene glycol monostearate | g | 1.0 |
| Methylparaben | g | 0.2 |
| Propylparaben | g | 0.1 |
| Perfume | q.s. | |
| Purified water | q.s | to g 100 |

EXAMPLE 5

| Face moisturizing cream | | |
|---|---|---|
| Mucopolysaccharide complex | g | 2.0 |
| Potassium glycerinizate | g | 0.1 |
| dl-α-tocopherol acetate | g | 0.05 |
| Extract of umbilical cord | g | 3.0 |
| Squalene | g | 8.0 |
| White vaseline | g | 3.0 |
| Amitel LG-OD (di-2-octyldodecyl-N-lauroyl-L-glutamate) | g | 5.0 |
| White wax | g | 1.0 |
| Glyceryl-monostearate | g | 1.0 |
| Propylene glycol monostearate | g | 4.0 |
| Sorbitane monostearate | g | 4.0 |
| N-acyl-L-sodium-glutamate | g | 0.2 |
| Solution of sorbitol (70%) | g | 5.0 |
| Glycerin | g | 2.0 |
| Stearic acid | g | 2.0 |
| Silicone resin | g | 0.5 |
| Propylparaben | g | 0.1 |
| Metylparaben | g | 0.2 |
| Perfume | g | 0.05 |
| Purified water | q.s | to g 100 |

EXAMPLE 6

| Anticellulitis cream | | |
|---|---|---|
| Stearic acid | g | 15.0 |
| Cetyl palmitate | g | 8.0 |
| Anhydrous lanolin | g | 4.0 |
| n-propyl p-oxybenzoate | g | 0.1 |
| Tween 80 | g | 2.5 |
| 1, 2-propylene glycol | g | 5.0 |
| Triethanolamine | g | 2.0 |
| Methyl p-oxybenzoate | g | 0.2 |
| Mucopolysaccharide complex | g | 0.3 |
| Escin | g | 1.0 |
| Tetrahydrofurfury-nicotinate | g | 0.05 |
| Distilled water | g | 61.0 |
| Extract of umbilical cord | g | 1.0 |
| Perfume | 3 | drops |

The weight ratio of the umbilical cord extract to the mucopolysaccharide complex contained in the formulations according to the present invention ranges from about 1:1 to about 15:1.

The formulations according to the present invention, which bind and block 5-α-dihydrotestosterone receptors, are characterized by a number of properties, as follows:

Remarkable hydrating effect on cutis, which avoids dehydration of the horny layer; retains water; prevents dandruff; reduces static electricity of the hair making it easier to comb and style; increases hair elasticity, making hair softer; form membranes having greater strength an elasticity than those obtained with other products such as polyvinyl alcohol, polyvinyl pyrrolidone or gelatine, and thus increases the hydrating effect and facilitates combing; improvement of the subcutaneous microcirculation through topical peripheral vasodilation and permanent action on the connective tissue; antibacterial activity due to a phenomenon of anionic repulsion with it typical of the extract of umbilical cord, with consequent hindrance of dandruff formation.

The totality of these properties and characteristics therefore permits extension of the use of the formulations according to the present invention to all of the morphological alterations of the subcutaneous connective tissues, which are characteristic of premature aging of skin in different cutaneous districts. Therefore, both active agents, conveniently chosen and mixed according to the present invention and rightly conveyed and combined with other substances, may be used in treating the various forms of chronic alopecia, particularly androgenetic and seborrheic alopecia; for treating dry and arid skins in order to avoid the formation of wrinkles or to attenuate wrinkles already formed; in topical treatment of cellulitis, owing to the vasodilating action and metabolic activation which favors the elimination of adipose cushions; as well as in ever other non-pathological skin problems caused by insufficient water content of the dermis.

The formulations according to the present invention are used for treating dermatological conditions by direct application of the formulations to the affect area. In the case of acne, the formulation is applied directly to the pustules or comedones. To treat androgenetic and seborrheic alopecia, the formulation is applied directly to the scalp. Topical application is continued at lease once daily until an improvement in the condition has been noticed, generally, from about one week to about six months. The amounts of active ingredients to be applied and the frequency of application are readily apparent to one skilled in the art without undue experimentation.

Berardesca et al., in a report published in *Int. J. Clin. Pharm. Res.* VIII(I) 6–73 (1988) describe the hydrating power of a topically applied mixture of glycosaminoglycans as evaluated by means of an electrical impedance method. The electrical parameters investigated, namely angle $\alpha$ and $R_\infty$ are related to the permeability and the hydration of deeper tissues. The study revealed a lowering of $\alpha$ levels after the application of the product, thus signifying an accumulation of electrical charges in the epidermis consistent with the penetration of glycosaminoglycans. After 15 days of treatment, significant reduction of $R_\infty$ levels was recorded.

Aging of the skin involves quantitative and qualitative variations in glycosaminoglycans. A large quantity of water is bound to non-sulfuric glycosaminoglycans in young skin, so that hyaluronic acid is of particular significance, whereas in elderly patients' skin there is a steady decrease in the tissues' water binding capacity. An increase in dermatansulfate and chondroitsulfates, accompanied by an inversion in the hyaluronic acid/chondroitinsulfuric acid ratio is found whenever there is a decrease in the concentration of hyaluronic acid which tends to depolymerize.

The study was carried out by applying both the mixture of natural mucopolysaccharides in a buffer of propylene glycol, sorbic acid, ethanol, distilled water, and the individual active components to the test skin. 1 ml $\times$ 10 cm$^2$ of the test substance was delicately applied to the forearm on an area of 5 $\times$ 10 cm. The active principles of the product were:

a) Thioglycan, a natural complex of animal origin, rich in heparin-like fractions an chondroitinsulfates;

b) HUCP, a natural complex extracted form the human umbilical cord, containing approximately 600 mg/cl of hyaluronic acid with a relative molecular mass of 2.8 million. Other substances present in HUCP are proteoglycans, glycoproteins, and polypeptides.

c) Thurfyl nicotinate, a low concentration cutaneous vasodilator.

The test was conducted on twenty male patients, aged between 25 and 35 years of age, with an average age of 28 years, in the best psychological conditions possible in order to avoid stress and psychogalvanic reflexes. Initial cutaneous impedance levels were recorded before the test substance was applied. After application, measurements were taken three times, once every thirty minutes. A check-up was performed after fifteen days' application in order to assess its long term effects.

The electrophysiological parameters examined were $R_\infty$, an expression of the dermal water content, and angle e related to the skin's barrier function. $R_\infty$ levels were measured in ohms, while $\alpha$ levels were measured in degrees.

The results relating to the comparison for a and $R_\infty$ obtained 30, 60, and 90 minutes after applying the product are given in Tables 3 and 4, respectively.

TABLE 3

Table 3 Mean levels (x) referred to $\alpha$ before treatment 30, 60 and 90 min. after applications: and after 15 days treatment (readings taken 24 hrs after the last application). The values are expressed in degrees.

| Base Levels | Minimum Levels (30, 60, 90 min. after applications) | Minimum Levels (after 15 days' treatment) |
|---|---|---|
| 173 | 125 | 170 |
| 175 | 126 | 170 |
| 169 | 168 | 157 |
| 161 | 142 | 168 |
| 111 | 139 | 176 |
| 95 | 67 | 170 |
| 177 | 153 | 152 |
| 135 | 132 | 141 |
| 147 | 139 | 40 |
| 178 | 103 | 162 |
| 171 | 129 | 169 |
| 173 | 128 | 170 |
| 168 | 167 | 166 |
| 162 | 143 | 169 |
| 115 | 142 | 120 |
| 99 | 95 | 102 |
| 138 | 133 | 143 |
| 145 | 140 | 140 |
| 176 | 134 | 164 | x = 152.10 ± 27.61  x = 131.80 ± 22.94  x = 150.90 ± 32.32
Significance: (base levels/min. levels) after 30, 60, 90 min. Students t = 2.53 ≤ 0.02.
after 15 days' treatment: Students t = 0.12 not significant

TABLE 4

Table 4 Mean levels (x) referred to R before treatment, 30, 60 and 90 min after applictions; and after 15 days' treatment readings taken 24 hrs after the last appliction). Measurements were taken in ohms

| Base Levels | Minimum levels (30, 60, 90 min. after applications) | Minimum levels (after 15 days' treatment) |
|---|---|---|
| 19 | 0 | 15 |
| 33 | 0 | 21 |
| 14 | 0 | 8 |
| 284 | 0 | 14 |
| 64 | 0 | 58 |
| 352 | 0 | 0 |
| 200 | 0 | 0 |
| 0 | 0 | 0 |
| 0 | 0 | 0 |
| 30 | 0 | 0 |
| 21 | 0 | 14 |
| 35 | 0 | 20 |
| 13 | 0 | 6 |
| 175 | 0 | 18 |
| 59 | 0 | 57 |
| 278 | 0 | 0 |
| 231 | 0 | 0 |
| 0 | 0 | 0 |
| 7 | 0 | 0 |

TABLE 4-continued

Table 4 Mean levels (x) referred to R before treatment, 30, 60 and 90 min after applictions; and after 15 days' treatment readings taken 24 hrs after the last appliction). Measurements were taken in ohms

| Base Levels | Minimum levels (30, 60, 90 min. after applications) | Minimum levels (after 15 days' treatment) |
|---|---|---|
| 26 | 0 | 0 |

$x = 92.05 \pm 114.49$  $x = 0.00 \pm 0.00$  $x = 11.60 \pm 17.53$
Significance: (base levels/min. levels)
After 30, 60, 90 min: Students $t = 3.60$ $p \leq 0.001$
After 15 days' treatment $t = 3.11$ $p \leq 0.001$ In the above tables, angle α is an expression of the degree to which the electrical barrier function is working properly. A constant and significant ($p < 0/02$) decrease was observed, as shown in Table 3 (18 cases out of 20) in the levels obtained during the study. In the light of these data, it is presumed that the product is able to influence the skin's electrical barrier. The harriet's decreased function would consequently induce penetration of the substance and a greater presence of electrical charges inside the epidermis. No statistically significant variations were observed with regard to angle α levels related to the measurements taken on each single component of the preparation.

With respect to R ∞, an expression of the resistance created by the dermis and the deeper tissues, Table 4 shows that, lo as compared with initially recorded levels, there was a significant and almost total drop to 0. This can be explained mainly on the basis of the remarkable vasodilating effect which is clinically evident in the widespread erythema produced by the thurfyl nicotinate contained in the product. In fact, the passage of the electrical current through the dermis is facilitated by increasing the blood flow in the skin's microcirculation, thus causing a decrease in the resistive levels. A persistent and significant reduction in the levels can be observed ($p < 0.0901$) when the initial levels are compared with the control levels recorded after fifteen days' treatment (cf. Table 4). Since the reading was conducted 24 hours after the last application, and there were no clinical signs of erythema present, the reduction observed is not attributable to vasodilation, but to the accumulation of water in the deeper layers.

These data obtained with a non-invasive in vivo method demonstrate the hydrating activity at deeper levels of natural mucopolysaccharides when applied topically on human skin. They are able to affect the skin's electrical barrier function and cause an increase in the water content in the dermis, which is observable as a decrease in the deep sensitive levels after prolonged topical administration in the absence of clinical signs of erythema. Although it is not possible to demonstrate whether this action is obtained directly, i.e., whether the product directly penetrates the skin, or whether this occurs indirectly with the formation of a surface film on the horny layer by means of nitrogen bindings between the hyaluronic acid and corneous cells, on the basis of the data obtained, the most reliable presumption is the former mechanism of action. This conclusion is arrived at because in the second case there should have been an increase in the water content in the corneous layer as well, which was not in fact observed during the course of this study.

43 patients suffering from defluvium and/or alopecia were submitted to a treatment with the formulation of Example 3.

The following parameters were evaluated : traction resistance and trichogram; behavior of symptoms such as seborrhea, pruritus, pityriasis; comprehensive objective judgement by the o investigator; subjective judgement by the patient and compliance to the treatment itself. The statistical elaboration of data has allowed to define the action of the topical product as favorable on defluvium (traction test and trichogram) and on seborrhea, proportionally to their entity; pruritus response was less evident, and pityriasis response was indifferent.

Materials and methods

The trial protocol has included a total number of 43 subjects (28 men and 15 women) suffering from defluvium and/or alopecia. These patients were treated with the topical product once a day for 12 days, then every other day until completion of a three month therapy course. The following parameters were considered before, during (every 30 days) and on completion of treatment: seborrhea, pruritus, pityriasis scaling, traction resistance, according to a five level judgement scale (very intense, intense, moderate, slight, absent).

A trichogram was carried out on beginning and completion of treatment, then on every control both investigator and patient were asked for a comprehensive judgement about efficacy, including the following evaluations: null, poor, sufficient, good, very good; the patient only was asked for a declaration about acceptance degree of the product under test.

Results

Table 5 reports the results concerning the four considered parameters, submitted to statistical elaboration by means of variance analysis.

Table 6 reports data concerning trichogram.

Table 7 reports comprehensive judgements about performed treatment, expressed by investigator and patients.

No sensitive effects were found during the trial; a few subjects (9%) noticed enhancement of pityriasis in the scalp, while two patients presented increase of pruritus or onset of pruritus which was absent before treatment (7%).

Besides clinical trial, an evaluation of irritating and sensitizing properties of the product was also conducted on healthy volunteers: open epicutaneous tests, read out after 4, 24, 28 and 48 hours, did not evidence any irritative reaction; the Schwartz Peck test (induced sensitization, followed by control tests after 14 days) has not evidenced onset of sensitatization in any subject.

Conclusion

The topical preparation of Example 3 has shown a generally favorable action after prolonged treatment for 60–90 days, particularly confirmed by trichogram results.

The compound has shown to be remarkably effective on seborrhea symptoms, above all where it is more marked, where as pruritus and scaling do respond to a lower extent. Therefore the activity of the topical product has been shown to be forable in cases of defluvium associated to seborrhea, whilst piatyriasis scaling appears to represent no indication for this treatment.

TABLE 5

| ENTITY | SYMPTOM: SEBORRHEA | | | | | |
|---|---|---|---|---|---|---|
| | PRE-TREATMENT | | | POST-TREATMENT | | |
| | TOTAL | | | TOTAL | | |
| VERY INTENSE | 22 | 20 | 2 | 6 | 6 | 0 |
| INTENSE | 6 | 2 | 4 | 3 | 2 | 1 |
| MODERATE | 9 | 5 | 4 | 17 | 10 | 7 |
| SLIGHT | 6 | 1 | 5 | 12 | 6 | 6 |
| ABSENT | 0 | 0 | 0 | 5 | 4 | 1 |
| MEAN SCORE | X: 2.95 | 3.36 | 2.2 X:1.79 | 1.85 | 1.53 | |

$= V_1 = 1 \quad V_2 = 54 \quad F = 19.22 \quad P < 0.05$
$= V_1 = 1 \quad V_2 = 28 \quad F = 3.87 \quad n.s.$

TABLE 6

| TRICHOGRAM | | | | | | |
|---|---|---|---|---|---|---|
| | ANAGEN | | TELOGEN + CATAGEN | | DYSTROPHIC HAIR | |
| | P | D | P | D | P | D |
| MALE (32) CASES | 16.56 | <37 | 59.57 | >38.19 | 23.87 | 24.81 |
| FEMALE (13 CASES) | 21.53 | <50.76 | 37.55 | >21.86 | 40.92 | 27.38 |
| TOTAL | 18.11 | <41 | 52.44 | >33.44 | 29.45 | 25.56 |

P = mean (x) % before treatment
D = mean (x) % after treatment

TABLE 7

| | COMPREHENSIVE JUDGEMENTS OF TENT (43 CASES) | | | | | | | | | | | | | |
|---|---|---|---|---|---|---|---|---|---|---|---|---|---|---|
| | NULL TOT. | | | POOR TOT. | | | SUFF.NT TOT. | | | GOOD TOT. | | | VERY GOOD TOT. | | |
| PHYSICIAN'S JUDGEMENT: | 9 | 6 | 3 | 11 | 6 | 5 | 12 | 6 | 6 | 10 | 9 | 1 | 1 | 1 | 0 |
| PATIENT'S JUDGEMENT: | | | | | | | | | | | | | | | |
| EFFICACY | 3 | 3 | 0 | 7 | 4 | 3 | 7 | 4 | 3 | 16 | 7 | 9 | 10 | 10 | 0 |
| ACCEPTANCE | 1 | 1 | 0 | 1 | 0 | 1 | 7 | 5 | 2 | 16 | 5 | 11 | 18 | 17 | 1 |

A technique has been developed in order to evaluate the action of a topical preparation by taking photographs before and after treatment of predetermined area of the scalp, both in alopecic patients and in healthy volunteers.

Materials and methods 18 subjects were submitted to investigation, aged between 23 and 32 years (average age: 25.88), divided into two groups (of both sexes) of 9 subjects, according to clinical data and a preliminary standard trichogram allocating subjects with not less than 25% telogen phase hair to the pathological group (B). In group A (subjects with trichogram within normal range), two subgroups were classified, based on the clinical data: subgroup A/1, consisting of 4 healthy subjects, and subgroup A/2, consisting of 5 subjects who complained of defluvium (without clinical correspondence) and/or seborrhea.

In group B, always based on the clinical data, two subgroups were indentified: namely B/1, consisting of 4 subjects with alopecia classified as 3rd and 4th degree according to Hamilaton (28), and B/2, consisting of 5 subjects with thinning hair and marked defluvium, but lower than the previously mentioned degrees.

No other local or systemic pathology was present in the subjects under investigation.

The topical preparation under study consisted of Thioglycoran, H.U.C.P., Thurfyl nicotinate, biotin, Sodium pantothenate, and was applied daily for 60 days.

Graphs 6, 7, 8 and 9 show distribution of the mean lengths and lengths of the sole elements in active growth phase of both groups A and B.

Conclusion

The morphometric image analysis has demonstrated itself as a valid and accurate method measurement.

The pre-treatment differences, between the groups under examination and particularly between subjects with and without hair pathology, were statistically confirmed from the different percentage of elements in active growth phase as well as by the measurement of mean lengths.

The differentation between rest phase hair and active growth phase hair, directly effected measuring the length at various intervals, appears to correspond to the real in-vivo image of the global hair growth phenomenon.

The single measurement of lengths and growth, with respect to the base value of only the active growth phase hair, is another parameter which is very useful.

The validity and sensitivity of the method appeared to be remarkable, above all in the comparative evaluation of the activity exerted by the treatment.

The topical preparation under test, 96 hours after cutting, induced statistically significant differences on the number of elements in active growth phase, on the mean hair length, on the length of the only elements in active growth phase, as well as on the growth values with respect to base growth of these elements.

The action of the topical product proved to be positive, but it should be noted that the application time was limited to two months, with immediate control at the end of treatment.

It is not possible to specify how the topical product exerts its action, and neither is it the purpose of this report: however, there is a probable stimulation at follicle level, which appears to induce elements to pass from the rest phase to the active growth phase, and the growth of the single element also appears to be strengthened.

Obviously, the objective of this investigation was neither to explain the possible mechanisms by which the above changes are obtained, nor to indicate which components of the product could be responsible for such changes.

TABLE 8

| N. SUBJECTS | | 1 | 2 | 3 | 4 |
|---|---|---|---|---|---|
| PARAMETERS BEFORE TREATMENT | | | | | |
| GROUP A | 9 | 84.69 | 1.673 ± 0.334 | 1.471 ± 0.543 | 1.078 |
| SUB-GR. A1 | 4 | 81.67 | 1.7635 ± 0.361 | 1.518 ± 0.6 | 1.130 |
| SUB-GR. A2 | 5 | 87.12 | 1.5812 ± 0.29 | 1.425 ± 0.473 | 1.037 |
| PARAMETERS AFTER TREATMENT | | | | | |
| GROUP B | 9 | 80.65 | 1.6455 ± 0.324 | 1.425 ± 0.533 | 1.165 |
| SUB-GR. B1 | 4 | 82.47 | 1.6267 ± 0.35 | 1.459 ± 0.514 | 1.183 |
| SUB-GR. B2 | 5 | 79.20 | 1.6487 ± 0.315 | 1.405 ± 0.543 | 1.15 |

PARAMETERS:
1: % hair in active growth phase in the single groups
2: after 96 hours, length of only the elements in active growth phase
3: mean length value of all elements, evaluated after hours

TABLE 9

| COMPARISONS | RESULT | PROBABILITY | STATISTICAL METHOD |
|---|---|---|---|
| 1. total mean lengths | | | |
| pre/post treatment | t = 3,5131 | P<0,01 | t for coupled data |
| inter-group pre-treatment | F = 3,3828 | P<0,05 | variance analysis |
| inter-group post treatment | F = 4,7734 | P<0,05 | variance analysis |
| 2. % active phase growth elements | | | |
| pre/post treatment | t = 4,89 | P<0,001 | t for coupled data |
| inter-group pre-treatment | F = 11,64 | P<0,005 | variance analysis |
| inter-group post treatment | F = 8,51 | P<0,005 | variance analysis |
| 3. lengths of only active growth phase elements | | | |
| pre/post treatment | t = 3,1552 | P<0,01 | t for coupled data |
| inter-group pre-treatment | F = 1,0326 | n.s.* | variance analysis |
| inter-group post treatment | F = 2,0384 | n.s.* | variance analysis |
| 4. growth with respect to base value | | | |
| pre/post treatment | t = 5,7718 | P<0,001 | t for coupled data |
| inter-group pre-treatment | F = 1,072 | n.s.* | variance analysis |
| inter-group post treatment | F = 0,01 | n.s.* | variance analysis |

ELECTROPHYSIOLOGICAL EVALUATION OF HYDRATING EFFECTS EXERTED BY A GLUCOSAMINOGLYCAN-CONTAINING PRODUCT FOR TOPICAL USE

After analysis of some aspects of their multiple interactions with protein and lipoprotein substrates, gluocosaminoglycans have aroused an increasing interest, and an essential role of these substances in mesenchymal metabolic process has been evidenced.

A special interest was found in interactions between acid mucopolysaccharide, in particular hyaluronic acid, and dermis power to retain water. In fact, the power of subcutaneous tissue to retain water is the more intense, the higher quantity of glucosaminoglycans is present. It is known that in young men's skin high contents of water are found, bound to acid mucopolysaccharide. In old men, where these substances tend to be reduced or depolymerized, a progressive decrease of the water contents is observed. In parallel, there is an increase of dermatan-sulfate, with inversion of the hyaluronic acid dermatan-sulfate ratio.

Glucosaminoglycans have been shown to be able to penetrate into the epidermis and reach the dermis, even after local application on the skins (1), and as a consequence a special attention has been focused b cosmetologists on these substances.

The study detailed below evaluated the hydrating effect of the composition according to the present invention containing a mixture of naturally occurring mucopolysaccharides, consisting of:

a) Thioglycoran: a naturally occurring mucopolysaccharide complex of animal origin, rich in heparin-like fractions and chondroitin-sulfate.

b) H.U.C.P.: a naturally occurring complex extracted from human umbilical cord, particularly featured by the presence of hyaluronic acid in a 600 ml/dl concentration, and a molecular weight corresponding to 2.8 millions. Moreover, in H.U.C.P., proteoglycans, glycoprotein and polypeptides are present.

c) Trafuryl nicotinate: a powerful vasodilator. The penetration and hydrating effect of this product have been evaluated by means of an "in vivo" non-invasive method, consisting of the determination of cutaneous bioelectrical paraeters (impedance).

By electrical impedance it is generally meant the expression of an obstacle opposed to passage of alternating current by a material (in this case, the skin). From a quantitative view point, it is possible to express this parameter using the ratio of applied voltage to the strength of current through the material.

Conclusion

A study was carried out of the in vivo bioelectrical effects on the cutaneous electrical barrier and the water contents in dermis, after topical application of a product containing nonsulfated glucosaminoglycans (KEVIS), and the study evidenced that said substances are able to exert effects on the cutaneous electrical barrier. For this reason, it may be assumed that the examined product is able to penetrate into the epidermis, thus inducing an increase of charges in this area, responsible for the reduction of the angle α. After continuous application of the substance, at dermal level a reduction of deep resistive values (Rint) is observed, which are compatible with an increase of dermal water contents, probably due to accumulation of mucopolysaccharide and hyaluronic acid at this level.

TABLE 10

Mean values (x), referred to α, in basal conditions and after application of the substance under test (minimum obtained value). Values are expressed in degrees. As indicated, a statistically significant reduction of the angle is present.

| BASAL VALUES | MINIMUM OBTAINED VALUE |
|---|---|
| 173 | 125 |
| 175 | 126 |
| 169 | 168 |
| 161 | 142 |
| 111 | 139 |
| 95 | 67 |
| 177 | 153 |
| 135 | 132 |
| 147 | 139 |
| 178 | 103 |
| 171 | 129 |
| 173 | 128 |
| 168 | 167 |
| 162 | 143 |
| 115 | 142 |
| 99 | 95 |
| 173 | 131 |
| 138 | 133 |
| 145 | 140 |
| 176 | 134 | x = 152.10 ± 27.58 Student "t" = 2.53
x = 131.80 ± 80.22.94 P< 0.02

TABLE 11

Mean values (x), referred to Rint, basal conditions and after use of the substance under test (minimum obtained value). statistically significant reduction of Rint values (determined in Ω is evidenced.

| BASAL VALUES | MINIMUM OBTAINED VALUE |
|---|---|
| 19 | 0 |
| 33 | 0 |
| 14 | 0 |
| 284 | 0 |
| 64 | 0 |
| 352 | 0 |
| 200 | 0 |
| 0 | 0 |
| 0 | 0 |
| 21 | 0 |
| 35 | 0 |
| 13 | 0 |
| 175 | 0 |
| 59 | 0 |
| 278 | 0 |
| 231 | 0 |
| 0 | 0 |
| 7 | 0 |
| 26 | 0 | x = 92.05 ± 114.49 Student "t" = 3.60
x = 0.00 ± 0.00 P <0.001

TABLE 12

Mean values (x), referred to Rint, in basal conditions and after a 15 day treatment. A statistically significant reduction of Rint (expressed in Ω) is observed.

| BASAL VALUES | VALUES AFTER 15 DAYS TREATMENT |
|---|---|
| 19 | 15 |
| 33 | 21 |
| 14 | 8 |
| 284 | 14 |
| 64 | 58 |
| 352 | 0 |
| 200 | 0 |
| 0 | 0 |
| 0 | 0 |
| 30 | 0 |
| 21 | 14 |
| 35 | 20 |
| 13 | 6 |
| 175 | 18 |
| 59 | 57 |
| 278 | 0 |
| 231 | 0 |
| 0 | 0 |
| 7 | 0 |
| 26 | 0 | x = 92.05 ± 114.49
x = 11.60 ± 17.53

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

What is claimed is:

1. A method for hydrating skin in a host in need thereof comprising administering to the skin of said host an effective amount of a composition comprising:
   (a) from about 0.1% to about 2.0% by weight of the total composition of mucopolysaccharides free of proteins and having a pH ranging from about 5 to about 7.5 in aqueous solution, a rotary power between about 0° and +15°, and a sulfur content about 6%;
   (b) from about 1% to about 3% by weight of the total composition of an aqueous extract of human umbilical cord wherein said extract produces a residue of about 2 to 3% at evaporation and is free from sulfur and having a pH of from about 5 to about 7, a viscosity at 30° C. of from 10 to 25 centistokes, a hyaluronic acid titre of from about 500 to about 700 mg/dl, and an ash content of about 0.1 to about 0.5%.
   (c) from about 0.05 to about 0.08% by weight of the total composition of tetrahydrofurfuryl nicotinate; and
   (d) pharmaceutically acceptable vehicles.

2. The method according to claim 1, wherein said mucopolysaccharides include hyaluronic acid which has a molecular weight between 2.5 million and 3 million daltons.

3. The method according to claim 1, wherein the composition has a weight ratio of said aqueous extract of human umbilical cord t said mucopolysaccharides ranges from about 1:1 to about 15:1.

4. The method according to claim 1, wherein the host is afflicted with a condition selected from the group consisting of acne, wrinkles, lipodystrophies, dermosclerosis, androgenetic alopecia, skin dystrophy, unaesthetisms, seborrheic alopecia, and hypertrichosis.

5. The method according to claim 4, wherein the host is afflicted with androgenetic and serborrheic alopecia and said composition is applied to the scalp.

6. The method according to claim 4, wherein the host is afflicted with skin dystrophy and unaesthetisms.

* * * * *

UNITED STATES PATENT AND TRADEMARK OFFICE
CERTIFICATE OF CORRECTION

PATENT NO. : 5,340,579
DATED : August 23, 1994
INVENTOR(S) : Casero, deceased

It is certified that error appears in the above-indentified patent and that said Letters Patent is hereby corrected as shown below:

On the title page, item [57]
    Line 2, replace "5-a" with --5-$\alpha$--";
    line 8, replace "to +15" with --0° to +15°"--;
    line 12, replace "DH" with --pH--;
    line 22, replace "dermosclorosis" with --dermosclerosis--.

Column 1, line 16, replace "one" with --the--;
               line 31, replace "Dart" with --part--;
    column 2, line 16, before "process" delete "o";
               line 33, replace "andro-genization" with --androgenization--;
               line 41, replace "ache" with --acne--;
    column 4, line 38, replace "lipodystrophics" with --lipodystrophies--;
               line 39, after "like" insert a period (.);
               line 45, replace "chose" with --chosen--;
               line 49, replace "hear" with --hair--;
    column 5, line 6, before "chon-" replace "g" with --C--;
               line 29, before "tissue" insert --much as that of the crumbled--;
               line 35, replace "propylpara" with --propyl-para--;
               line 68, replace "0..1 M" with --0.1 M--;
    column 6, line 26, replace "weighted" with --weighed--;

UNITED STATES PATENT AND TRADEMARK OFFICE
CERTIFICATE OF CORRECTION

PATENT NO. : 5,340,579
DATED : August 23, 1994
INVENTOR(S) : Casero, deceased

It is certified that error appears in the above-indentified patent and that said Letters Patent is hereby corrected as shown below:

line 27, replace "representatively" with --respectively--;
                line 29, replace "dried" with --drier--;
                between line 38 and Table 1", insert --The results obtained are shown in Table 1.--;
                line 59, replace "DO" with --D)--;
                line 61, replace "0.1 g" with --1.0 g--;
                line 65, replace "weighted" with --weighed--;
        column 7, lines 1-2, delete "and schematically illustrated in FIG. 5";
                line 5, Table 2, insert in the third column --A--, in the fourth column --B--, in the fifth column --C-- and in the sixth column --D--;
                line 28, replace "mixture" with --mixtures--;
                line 31, after "such as" insert --vasodilators--;
                line 40, replace "androgenitic" with --androgenetic-- and "seborrhec" with --seborrheic--;
                line 47, replace "pantothenatemg" with --pantothenate--;
                line 49, delete "mg";
                line 58, replace "umbilica" with --umbilical--;
                line 62, replace "monoaurate" with --monolaurate--;
        column 8, line 7, replace "glycerinizate" with --glycyrrhizinate--;
                line 37, replace "Tetrahydrofurury-nicotinate" with --Tetrahydrofurfuryl-nicotinate--;

UNITED STATES PATENT AND TRADEMARK OFFICE
CERTIFICATE OF CORRECTION

PATENT NO. : 5,340,579

DATED : August 23, 1994

INVENTOR(S) : Casero, deceased

It is certified that error appears in the above-indentified patent and that said Letters Patent is hereby corrected as shown below:

line 54, before "elasticity" replace "an" with --and--;

line 61, replace "with it" with --which is--;

column 9, line 19, replace "lease" with --least--;

line 44, replace "chondroitsulfates" with --chondroitinsulfates--;

line 60, replace "mg/cl" with --mg/dl--;

column 10, line 9, replace "angle e" with --angle $\alpha$--;

line 12, replace "a" with --$\alpha$--;

line 48, before "readings" insert --(--;

column 11, line 21, replace "harriet's" with --barrier's--;

line 31, delete "lo";

column 12, line 7, before "investigator" delete "o";

line 66, replace "forable" with --favorable--;

line 67, replace "piatyriasis" with --pityriasis--;

column 13, line 30, heading of Table 7" replace "TENT" with --TREATMENT--;

line 62, replace "Hamilaton" with --Hamilton--;

column 14, delete the entire paragraph spanning lines 17-19, starting with "Graphs 6, 7, 8" and ending with "groups A and B";

column 15, line 22, parameter 3, before "hours" insert --96--;

UNITED STATES PATENT AND TRADEMARK OFFICE
CERTIFICATE OF CORRECTION

PATENT NO. : 5,340,579
DATED : August 23, 1994
INVENTOR(S) : Casero, deceased

Page 4 of 4

It is certified that error appears in the above-indentified patent and that said Letters Patent is hereby corrected as shown below:

```
        column 16, line 1, replace "b" with --by--;
                  line 12, replace "ml/dl" with --mg/dl--;
                  line 16, replace "Trafuryl" with
--Thurfyl--;
                  line 20, replace "paraeters" with
--parameters--;
        column 17, line 32, replace "statistically" with
--Statistically--;
                  line 33, replace "Ω" with --Ω)--.

Column 18, line 57, after "cord" replace "t" with
--to--;
                  line 58, replace "ranges" with
--ranging--.
```

Signed and Sealed this

Twenty-first Day of March, 1995

BRUCE LEHMAN

*Attest:*

*Attesting Officer*     *Commissioner of Patents and Trademarks*